(12) United States Patent
Klangby et al.

(10) Patent No.: US 10,246,740 B2
(45) Date of Patent: Apr. 2, 2019

(54) SELECTIVE AMPLIFICATION OF DESIRED NUCLEIC ACID REGIONS IN A TARGET SEQUENCE

(71) Applicant: Devyser Holding AB, Hägersten (SE)

(72) Inventors: Ulf Klangby, Hägersten (SE); Anders Hedrum, Hägersten (SE); Steffen Heim, Hägersten (SE)

(73) Assignee: Devyser Holding AB, Hägersten (SE)

( * ) Notice: Subject to any disclaimer, the term of this patent is extended or adjusted under 35 U.S.C. 154(b) by 0 days.

(21) Appl. No.: 16/063,227

(22) PCT Filed: Jan. 27, 2017

(86) PCT No.: PCT/EP2017/051793
§ 371 (c)(1),
(2) Date: Jun. 15, 2018

(87) PCT Pub. No.: WO2017/129756
PCT Pub. Date: Aug. 3, 2017

(65) Prior Publication Data
US 2018/0371528 A1 Dec. 27, 2018

(30) Foreign Application Priority Data
Jan. 27, 2016 (EP) .................................... 16152951

(51) Int. Cl.
*C12Q 1/68* (2018.01)
*C12Q 1/686* (2018.01)
*C12Q 1/6848* (2018.01)

(52) U.S. Cl.
CPC .......... *C12Q 1/686* (2013.01); *C12Q 1/6848* (2013.01); *C12Q 2525/155* (2013.01); *C12Q 2525/161* (2013.01); *C12Q 2537/143* (2013.01); *C12Q 2537/159* (2013.01)

(58) Field of Classification Search
None
See application file for complete search history.

(56) References Cited

U.S. PATENT DOCUMENTS

| 9,605,305 B2 | 3/2017 | Wang et al. |
| 10,011,869 B2 | 7/2018 | Wang et al. |
| 2017/0107561 A1 | 4/2017 | Wang et al. |

FOREIGN PATENT DOCUMENTS

WO  WO 2008/033442  3/2008

*Primary Examiner* — Samuel C Woolwine
(74) *Attorney, Agent, or Firm* — James S. Keddie; Bozicevic, Field & Francis LLP

(57) ABSTRACT

A method and kit for selective amplification of desired amplicons in a two-stage polymerase chain reaction is provided. The method and kit uses target primers comprising mismatch control sequences; wherein any pair of primers that flank a desired amplicon sequence have non-matching mismatch control sequences. and any pair of primers that flank an undesired amplicon sequence have matching mismatch control sequences.

17 Claims, 12 Drawing Sheets
Specification includes a Sequence Listing.

Unwanted short products

Wanted longer products

SELECTIVE AMPLIFICATION OF DESIRED NUCLEIC ACID REGIONS IN A TARGET SEQUENCE

CROSS-REFERENCE TO RELATED APPLICATIONS

This application is a § 371 national phase of International Application No. PCT/EP2017/051793, filed on Jan. 27, 2017, which claims the benefit of European Patent Application No. 16152951.6, filed on Jan. 27, 2016, which applications are incorporated by reference herein.

FIELD OF THE DISCLOSURE

The present disclosure is in the field of nucleic acid analysis, in particular related to polymerase chain reactions and subsequent massive parallel sequencing.

BACKGROUND

During several decades, dideoxy DNA sequencing ("Sanger" sequencing, Sanger et al (1977), Proc Natl Acad Sci USA 74:5463-5467) has been used as the standard sequencing technology in most genetic laboratories. Throughput is limited when using Sanger sequencing, since the process is performed on single molecules of target sequence. The search for a faster, cheaper and more accurate sequencing method, which adds the advantage of high throughput, has led to the development of several new techniques currently denoted "massive parallel sequencing" (MPS) or "next-generation sequencing" (NGS).

The introduction of MPS methods have changed the paradigm of DNA sequencing (Mardis (2008), Trends Genet 24:133-141; Shendure & Ji (2008), Nat. Biotechnol 26:1135-1145). MPS methods enable the parallel processing of hundreds of thousands to millions of DNA templates in parallel, resulting in high throughput and a low cost per base of the generated sequence. The introduction of MPS methods furthermore allows the user to rapidly sequence entire complex genomes such as the human genome.

Nevertheless, large scale routine sequencing of the whole complex human genome in its entirety is not yet feasible for diagnostic use because of the cost and time are still too great. Routine sequencing of the human genome for diagnostic use requires at least 100-1000-fold coverage of each nucleotide, resulting in the need to sequence and process 300-3000 Gb of sequencing data per patient. With available MPS methods, this would require several sequencing runs/patient and cost tens of thousands of dollars. In addition to the economic burden, it would require massive data processing and data storage capabilities that would place a substantial burden on the informatics infrastructure of a genetic laboratory.

As a consequence, several methods aiming to simplify the process and enrich regions of interest for e.g. sequencing, i. e. target enrichment methods, have been developed. Target enrichment methods are used to define genomic regions that can be selectively captured and enriched from a DNA sample before sequencing. Re-sequencing only those genomic regions that are enriched is much more time- and cost-effective than whole genome sequencing, and the resulting data is considerably less cumbersome to analyze and requires less data storage capabilities.

Known target enrichment methods include molecular inversion probes (MIP), on-array- and in solution-hybrid capture and polymerase chain reaction (PCR). Each are discussed separately below.

Molecular Inversion Probes (MIP):

MIP are modified padlock probes. When a probe is hybridized to a corresponding genomic target, there is a gap at one or more nucleotide positions. A design where the probe lacks a complementary nucleotide at e.g. a single-nucleotide polymorphism (SNP) location can be used for detection and identification of the polymorphism. If the gap of the hybridized probe is more than a single nucleotide, the probes are in general termed "connector inversion probes" (CIP). The advantage of using this type of probes is that they can be used for SNP genotyping, copy number variation (CNV) analysis, and for detection of allelic imbalances. The probes can be designed such that they contain tag sequences for identification of the probe, as well as primer sequences for sequencing the target region. As compared to other target enrichment techniques, molecular inversion probes demonstrate a good specificity but may show some variability in performance between different probes within assays.

On-Array and in-Solution Hybrid Capture:

If one is interested in capturing genomic regions using in-solution capturing technique, one may use a number of oligonucleotides (probes) and hybridize them to fragmented genomic DNA in-solution (as opposed to hybrid or array based methods). The probes, which may be attached to paramagnetic beads, hybridize to the DNA of interest. Following hybridization, the beads containing probes and complementary DNA-fragments can be separated, and non-bound DNA material is removed by washing the beads. Following removal from the beads, the DNA can be sequenced using Sanger sequencing or MPS methods. One advantage of this technique as compared to array-based techniques is the improved target enrichment due to the high probe/target ratio. This may, however, have implications on the attempts to lower the costs for MPS.

Polymerase Chain Reaction (PCR):

PCR has been widely used for pre-sequencing sample preparations (Saiki et al (1988), Science 239:487-491), as it is well compatible with a traditional Sanger sequencing based approach. PCR is also compatible with any current MPS platform. However, in order to make full use of the high throughput enabled by the MPS technology, a large number of PCR amplification products ("amplicons") must be processed and sequenced together. Multiplex PCR allows the user to generate multiple different PCR amplicons from a single PCR reaction, and is particularly useful during target enrichment for MPS. Multiplex PCR may be difficult to perform, because the simultaneous use of multiple primer pairs frequently generates a high level of non-specific amplification, caused by an interaction between primers (Cho et al (1999), Nat Genet 23:203-207; Wang et al (1998), Science 280:1077-1082). Various methods of overcoming non-specific amplification in multiplex PCR have been developed (Fredriksson et al (2007), Nucleic Acids Res 35:e47; Meuzelaar et al (2007), Nat Methods 4:835-837; Varley & Mitra (2008), Genome Res 18:1844-1850; U.S. Pat. No. 5,677, 152).

For many MPS platforms, there is an upper limit to the length of DNA fragment that can be sequenced in a single run. For this reason, many target DNA fragments must be divided into shorter amplicons, each represented by a specific primer pair, in order to obtain a continuous DNA sequence after data analysis. In order to maximize throughput, it is often also necessary not to use too short PCR amplicons as these will reduce the total number of potential base reads in a sequencing run.

In order to obtain full sequencing coverage of a defined region within the human genome, amplicons may be designed to overlap using primer tiling design. In order to obtain efficient PCR amplification and optimal amplicon lengths, and to avoid extensive non-specific amplification, it is currently necessary to divide multiplex PCR reactions into several separate reactions when using overlapping primer design. In this way, the actual overlapping designs are separated into different PCR reactions. If a clinical sample needs to be divided into several different multiplex PCR reactions, the risk for sample mix-up and sample contamination is increased. The use of multiple PCR reactions for the analysis of a clinical sample can also be a problem when the amount of DNA available for the analysis is limited.

Digital PCR has been proposed as a suitable method for MPS library preparation. Digital PCR is based on clonal amplification of nucleic acids and requires highly specialized equipment in order to be efficiently performed. Digital PCR is also considered to be prone to error in the hands of inexperienced users (Sykes et al (1992), BioTechniques 13(3):444-9; Perkel (2015), BioTechniques 58 (5): 217-21, Pekin et al (2011), Lab on a Chip 11(13):2156-66). Sample preparation by digital PCR requires more available DNA for the analysis as compared to a single reaction PCR.

There is a need in the art for methods that improve multiplex PCR reactions in general. There is in particular a need for methods that address the problem of non-specific and/or unwanted amplification in multiplex PCR reactions in several stages, for example during target amplification for genetic diagnostic applications, library preparation, re-sequencing and other situations.

SUMMARY OF THE DISCLOSURE

One object of the disclosure is to address this need by enabling selective amplification of desired nucleic acid regions in a target sequence.

Another object is to provide a method which introduces differences in self-hybridization properties of nucleic acid fragments as a tool to select between desired and undesired amplification products.

Another object is to provide a method that enables selective PCR amplification of overlapping short amplicons in a single reaction.

Another object is to provide a method that will provide short overlapping amplicons covering long continuous stretches of DNA in a single reaction.

These objects, and others that are evident to the skilled person from the teachings herein, are met by the different aspects of the disclosure as defined herein and in the appended claims.

Thus, in a first aspect, the disclosure provides a method for selective amplification of desired amplicons in a two-stage polymerase chain reaction, comprising the steps of:
  providing a target genetic material;
  denaturing the target genetic material;
  adding a set of target primers under conditions allowing annealing of primers to the target genetic material;
    each primer in said set of target primers comprising
      a target specific sequence,
      a mismatch control sequence, and
      a generic hybridization sequence;
    said generic hybridization sequence being identical in each target primer;
    said mismatch control sequence and generic hybridization sequence being in close proximity to each other; and
    said set of target primers comprising at least two primer pairs adapted for amplification of at least two overlapping desired amplicons in the target genetic material, such that there is a possibility of obtaining at least one undesired amplicon in the region of overlap;
    said set of target primers being further characterized in that any pair of primers that flank a desired amplicon sequence have non-matching mismatch control sequences, while any pair of primers that flank an undesired amplicon sequence have matching mismatch control sequences;
  carrying out a first multiplex polymerase chain reaction, resulting in overlapping amplicons corresponding to different possible pair-wise combinations of primers in the first set of primers, said overlapping amplicons being maintained under conditions such that they self-hybridize through base-pair coupling between the complementary sequences resulting from the generic hybridization sequence in each primer;
  treating said overlapping amplicons under selection conditions that are such that desired amplicons denature because of non-complementary sequences resulting from the non-matching mismatch control sequences, while undesired amplicons stay self-hybridized because of additional complementary sequences resulting from the matching mismatch control sequences;
  adding generic primers, each comprising a sequence which is complementary to the generic hybridization sequence;
  carrying out a second polymerase chain reaction, resulting in the selective amplification of desired amplicons.

In a second aspect, the disclosure provides a kit for carrying out the method, which comprises the necessary key reagents and instructions for putting the method into practice. In this aspect is provided a kit for carrying out the method according to the first aspect, comprising:
  a set of target primers;
    each primer in said set of target primers comprising
      a target specific sequence,
      a mismatch control sequence, and
      a generic hybridization sequence;
    said generic hybridization sequence being identical in each target primer;
    said mismatch control sequence and generic hybridization sequence being in close proximity to each other; and
    said set of target primers comprising at least two primer pairs adapted for amplification of at least two overlapping desired amplicons in a target genetic material, such that there is a possibility of obtaining at least one undesired amplicon in the region of overlap;
    said set of target primers being further characterized in that any pair of primers that flank a desired amplicon sequence have non-matching mismatch control sequences, while any pair of primers that flank an undesired amplicon sequence have matching mismatch control sequences;
  generic primers, each comprising a sequence which is complementary to the generic hybridization sequence; and
  instructions for carrying out the method according to the first aspect using said primers.

Thus, the disclosure concerns situations where a first PCR reaction is carried out, and the resulting amplified fragments, or amplicons, are used as templates in a second PCR reaction. Specifically, said first PCR reaction is such that it has the possibility of generating at least two alternative amplicons, one of which is less desired than the other with regard to use as a template for the second reaction. One of the underlying insights of this disclosure is that it is possible to promote the use of the desired amplicon as template, and suppress the use of the undesired amplicon. This is done by enhancing the intrinsic tendency of amplicons from the first PCR reaction to self-hybridize at regions of sequence complementarity. All amplicons from the first PCR reaction will have complementary sequences due to the presence of a generic hybridization sequence (which is used for primer annealing in the second PCR). Under normal PCR reaction conditions, this will lead to the amplicons forming stem-loop structures after the first PCR reaction. In order for such stem-loop structures to serve as templates for a second PCR reaction, the self-hybridized stretch of sequence needs to denature in order to allow the annealing of generic primers at the same sequence. Under normal conditions, such denaturing would occur to the same extent regardless of whether the amplicon is desired or undesired as template. This is especially so in case the reaction vessel already contains the generic primers, because these will compete for base pairing with the generic sequence. The disclosure herein allows to adjust the strength of the self-hybridization in the stem-loop structures that are formed by the amplicons from the first PCR reaction, by ensuring that undesired amplicons form stem-loop structures that are less readily denatured than the corresponding stem-loop structures formed by desired amplicons. This is done by inserting, into the primers for the first PCR reaction, a relatively short sequence designed to confer extra self-complementarity into undesired amplicons, while no such extra self-complementarity is provided to desired amplicons. This short sequence is denoted "mismatch control sequence" in the present disclosure. Regions of target sequence that one does not desire as an end result after the second PCR are flanked by primers (for the first PCR) containing matching mismatch control sequences, because such matching sequences will enhance the self-hybridization of the resulting amplicons and make them less accessible to primer annealing in the beginning of the second PCR. Conversely, regions of target sequence that are desired as end result, e.g. for sequencing, detection or any other purpose, are flanked by first PCR primers that contain non-matching mismatch control sequences. One embodiment of the disclosed method is presented schematically in FIG. 9.

The skilled person will realize that it is possible to benefit from the general principle of the disclosure in several different set-ups, which are all intended to be encompassed by the appended claims. This applies for example to the order of steps in the method. It is possible to carry out the two PCR stages in different reaction vessels, but it may be equally preferable to carry them out in the same reaction vessel. In one embodiment, the generic primers (i.e. the primers for the second PCR reaction) are added after the first PCR reaction. In another embodiment, wherein the reactions are carried out in the same reaction vessel, the generic primers are added before the first PCR reaction, for example at the same time as the target primers (i.e. the primers for the first PCR reaction) are added.

The same reasoning applies to the reaction conditions of the PCR reactions. These may be tailored by the skilled person such that the appropriate annealing and denaturation conditions for the steps of the disclosed method are present. In particular, the conditions at the beginning of the second PCR reaction need to be such that strand separation (denaturation) and generic primer annealing is made possible onto amplicons with non-matching mismatch control sequences, i.e. those that have a shorter self-complementary stretch of sequence, while generic primer annealing is inhibited at amplicons with matching mismatch control sequences, i.e. those that have a longer self-complementary stretch of sequence. The calibration of such conditions, with regard to factors such as temperatures for denaturation, annealing and extension temperatures, as well as the concentration of additives such as $Mg^{2+}$ ions, DMSO, betaine and formamide, would depend on the specific circumstances and aims in each case, but finding them would be within the capabilities of a person skilled in the established art of PCR technology (see for an overview of PCR technology for example Bartlett and Stirling (2003), PCR Protocols. Methods in Molecular Biology 226:3-6, or Sambrook and Russel (2001), Molecular Cloning: A Laboratory Manual (3rd ed.). Cold Spring Harbor, N.Y.: Cold Spring Harbor Laboratory Press. ISBN 0-879-69576-5. Chapter 8: "In vitro Amplification of DNA by the Polymerase Chain Reaction").

With regard to the target primers, these comprise three different stretches of sequence with different functions in the context of the disclosure. These three may be distinct and follow each other, either directly or in close proximity. Thus, the target specific sequence may be followed by the mismatch control sequence, which is then in turn followed by the generic hybridization sequence. In some embodiments, however, these three functionally defined stretches of sequence may overlap. This is for example the case if one or more bases of the mismatch control sequence are also complementary to the target sequence, so that one of the ends of the target specific sequence fulfils the function of mismatch control as well as target binding. It is also possible that mismatch control is provided by mismatches introduced throughout either or both of the target specific sequence and the generic hybridization sequence, which means that the three different sequence elements are actually completely or partly interspersed along the target primer oligonucleotide. The precise definition of a target primer for use in the disclosed method and kit is not critical, as long as it allows for different self-hybridization strength depending on whether or not the flanked target sequence is desired or undesired for amplification. For the purposes of the following discussion concerning the length of the different sequences, it is easier to consider these as being distinct sequence segments, but, again, it is also possible to use primers in which the function of mismatch control is intermingled within the target specific or generic hybridization sequences.

In one embodiment, the total length of a target primer in the set is from about 7 to about 200 nucleotides, always provided that the necessary functions of target binding, mismatch control and generic hybridization are present.

In one embodiment, in which the mismatch control sequence is a distinct sequence, the length of the mismatch control sequence is from 1 to 7 nucleotides, such as from one to five, from one to three, for example from one to two nucleotides. The length is not critical but depends on other factors, in particular the annealing and denaturation conditions in the initial stages of the second PCR reaction.

The length of the generic hybridization sequence is not critical either, as long as it allows for annealing and priming by the corresponding generic primers in the second PCR reaction. In one embodiment, the generic hybridization sequence is from 1 to 75 nucleotides in length, for example from 3 to 75 nucleotides, from 5 to 60 nucleotides, from 5 to 40 nucleotides or from 5 to 20 nucleotides, such as from 10 to 20 or from 7 to 15 nucleotides. The skilled person is able to design suitable generic hybridization sequences based e.g. on base pairing strength etc, wherein the use of stronger base pairing could allow for a shorter hybridization sequence, while the use of weaker base pairing could allow for a longer hybridization sequence.

With regard to the target specific sequence, this needs to be sufficiently long to ensure specific hybridization at the desired region of target nucleic acid. Again, the skilled person is aware of the design considerations involved, and is able to design such primers without undue experimentation. In one embodiment, the target specific sequence is from 5 to 100 nucleotides in length, for example from 8 to 70 nucleotides, from 10 to 50 nucleotides or from 10 to 40 nucleotides, such as from 15 to 30 nucleotides in length, for example from 18 to 25 nucleotides, for example from 20 to 25 nucleotides.

Typically, but not always, the target specific sequence is complementary to a diagnostic sequence in the target genetic material, so that detection or sequencing of this sequence is of diagnostic or clinical interest.

In one embodiment, at least some of the primers involved in the different reactions are detectably labeled, for example in order to follow the reactions and/or detect the end products. The skilled person is aware of different options for labeling nucleotide molecules, e.g. with fluorescent labels, and may do so without undue experimentation.

In one embodiment, the disclosed method is used in the preparation of a sequence library from a target genetic material consisting of genomic DNA to be sequenced. This sequence library may subsequently be used for nucleic acid sequencing. In such applications, the generic primers, used in the second PCR reaction of the disclosed method and contained in the disclosed kit, may further comprise adapter sequences for the desired sequencing method used. Also, in one such embodiment, the disclosed method further comprises the step of sequencing the desired amplicons resulting from the two stages of PCR amplification. In one specific embodiment, said sequencing is carried out using massively parallel sequencing. Suitably, in one embodiment, the generic primers also comprise index sequences so that the amplicon products may be identified if pooled with amplicons from separate reactions performed on other target genetic material or on samples from different individuals. Thus, in these embodiments, it is possible to use the disclosed method and kit to obtain a collection of patient specific, target tagged, indexed, purified and standardized target specific amplicons in the form of a patient specific target library, which can then be pooled together with target specific libraries from other patients or analyzed alone before sequencing, e.g. massively parallel sequencing, is performed. A library pool can be made from several patient samples for the same target or multiple targets for the same patient or a combination of both as long as the indexing sequences used in the second PCR reaction are unique for each patient.

While the invention has been described with reference to various exemplary aspects and embodiments, it will be understood by those skilled in the art that various changes may be made and equivalents may be substituted for elements thereof without departing from the scope of the disclosure herein. In addition, many modifications may be made to adapt a particular situation to the teachings of the invention without departing from the essential scope thereof. Therefore, it is intended that the invention not be limited to any particular embodiment contemplated, but that it include all embodiments falling within the scope of the appended claims.

BRIEF DESCRIPTION OF THE FIGURES

FIG. 12 is a schematic illustration of the possible products of multiplex PCR amplification of a stretch of target DNA, showing the short, unwanted product eliminated by the method disclosed herein, the longer, desired amplicons, and the amplicons obtained upon read through.

EXAMPLES

The following Examples illustrate embodiments of the disclosure as put into practice in different settings.

Example 1

Establishment of the Basic Principles of the Disclosed Method

Materials and Methods

This example involved carrying out two separate experiments, each comprising a first target tagging (TT) PCR reaction performed on purified human genomic DNA. The TT PCR was followed by a second indexing (ID) PCR reaction step. The PCR amplicons generated in the TT PCR reaction were diluted 1:50 in water before ID PCR was performed.

The TT PCR primers were designed to include a 3' target specific part of about 20-25 nucleotides and a generic hybridization sequence at the 5' end of the oligonucleotide. The ID PCR primers were designed to include an oligonucleotide sequence at the 3' end which was able to anneal specifically to the generic hybridization sequence present in all TT PCR primers. The ID primers further included specific sequencing adaptors and index sequences to allow MPS and index recognition. In this example, the sequencing adaptor sequences used were the "Ion A" and "Ion P1" adaptor sequences specifically designed to allow sequencing on the Thermo Fisher Ion PGM MPS instrument.

Figure 1:
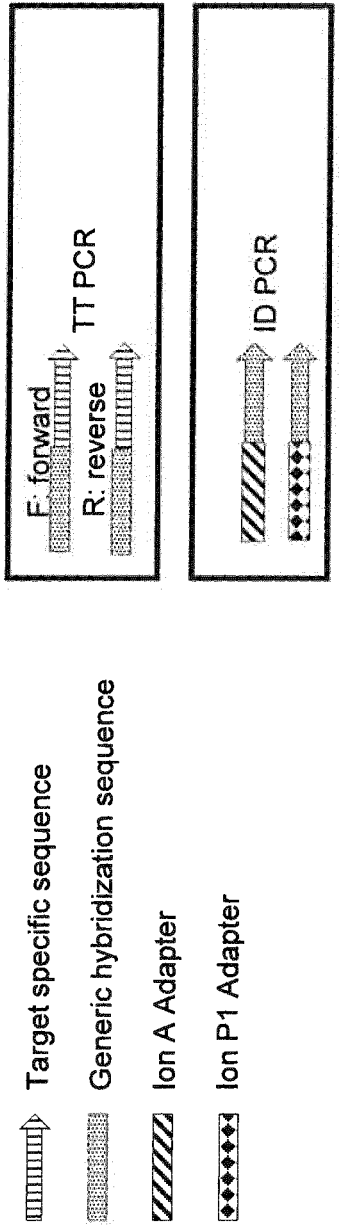
FIG. 1 is a schematic illustration of the primer constructs disclosed herein and used in various embodiments of the method.
Figure 2:
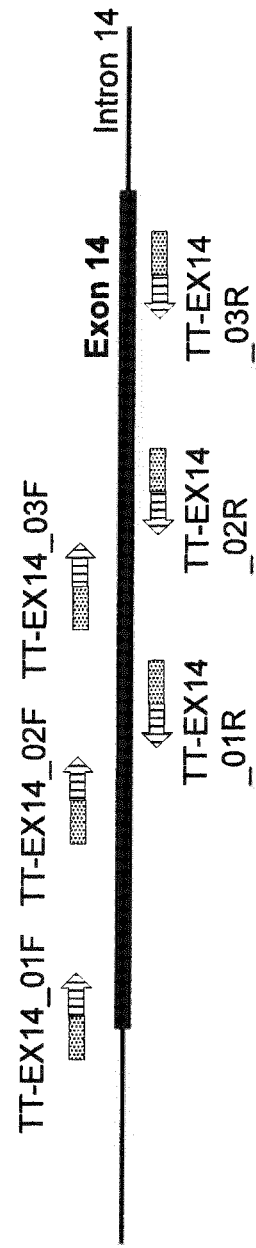
FIG. 2 is a schematic illustration of the primer pairs used in Example 1 as well as their positions relative to the target sequence, exon 14 of the human CFTR gene.

FIG. 1 depicts the primers used schematically, and FIG. 2 shows, again schematically, their relationship to the target sequence, exon 14 of the CFTR gene. The nucleotide sequences of the primers used are presented below in Table 1, wherein the hybridization part of the respective oligonucleotide is in underlined and bold typeface.

TABLE 1

Oligonucleotide primers for multiplex PCR in two stages

| SEQ ID NO: | Designation | Sequence | 5' Label |
|---|---|---|---|
| 1 | TT-EX14_02F (P51) | GCTCTTCCGATCTGCAGTCTGTCC TGAACCTGAT | — |
| 2 | TT-EX14_02R (P52) | GCTCTTCCGATCTGCCAGTTTCTT GAGATAACCTTCTTGA | FAM |
| 3 | TT-EX14_01F (P57) | GCTCTTCCGATCTTTCCATTGTGC AAAAGACTCCCTTA | — |
| 4 | TT-EX14_03R (P60) | GCTCTTCCGATCTGGAAGAGATA TGTCCATTGCAAAAGAA | HEX |
| 5 | ID-Ion P1 (P43) | CCACTACGCCTCCGCTTTCCTCTC TATGGGCAGTCGGTGATGCTCTTC CGATCT | HEX |
| 6 | ID-Ion A (P44) | CCATCTCATCCCTGCGTGTCTCCG ACTCACAGAAGGAACGATGCTCTT CCGATCT | FAM |

Figure 3:
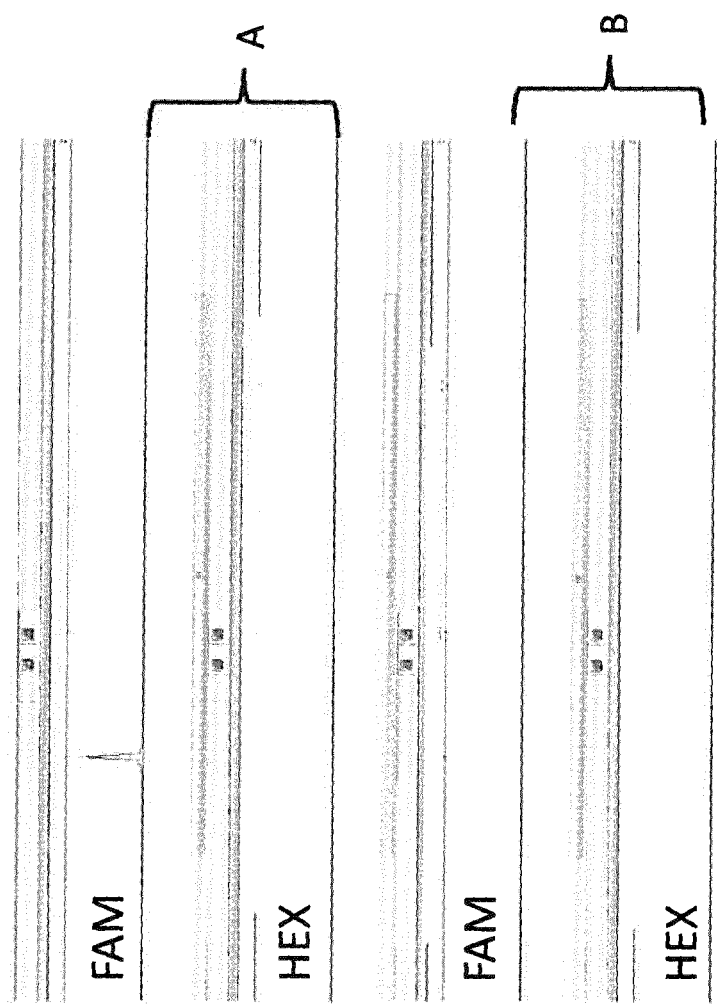
FIG. 3 shows chromatograms from detection of A) TT PCR fragments and B) ID PCR fragments, using capillary electrophoresis after use of the primer pair TT-EX14_02F/TT-EX14_02R, followed by the primer pair ID-Ion P1 and ID-Ion A.

In the first experiment, the primer combination TT-EX14_02F/TT-EX14_02R, specific for sequences within the CFTR exon 14 was used for TT PCR as the first stage PCR reaction. After completion of this PCR program, the resulting solution was diluted 50-fold, and 2 µl of the dilution were added as a template in the following ID PCR second stage multiplex reaction. ID PCR was performed using the ID-Ion P1 and ID-Ion A primers. Both the TT and the ID PCR reactions were analyzed by capillary electrophoresis detection of fluorescently labeled, amplified PCR fragments, and the obtained chromatograms are presented as FIG. 3.

A second similar experiment was performed, but using instead the two primer couples TT-EX14_01F/TT-EX14_02R and TT-EX14_02F/TT-EX14_03R in two separate first stage TT PCR reactions, simulating a multiplex PCR with overlapping target sequences. Using these two primer pairs, and with reference to FIG. 2, the two desired amplicons are the regions flanked by i) forward primer TT-EX14_01F and reverse primer TT-EX14_02R and ii) forward primer TT-EX14_02F and reverse primer TT-EX14_03R, respectively. In a true multiplex PCR reaction, it would theoretically also be possible that the TT PCR generates an undesired amplicon in the region of overlap, i.e. the region flanked by forward primer TT-EX14_02F and reverse primer TT-EX14_02R, i.e. the very product obtained by these two primers in the first experiment.

Figure 4:
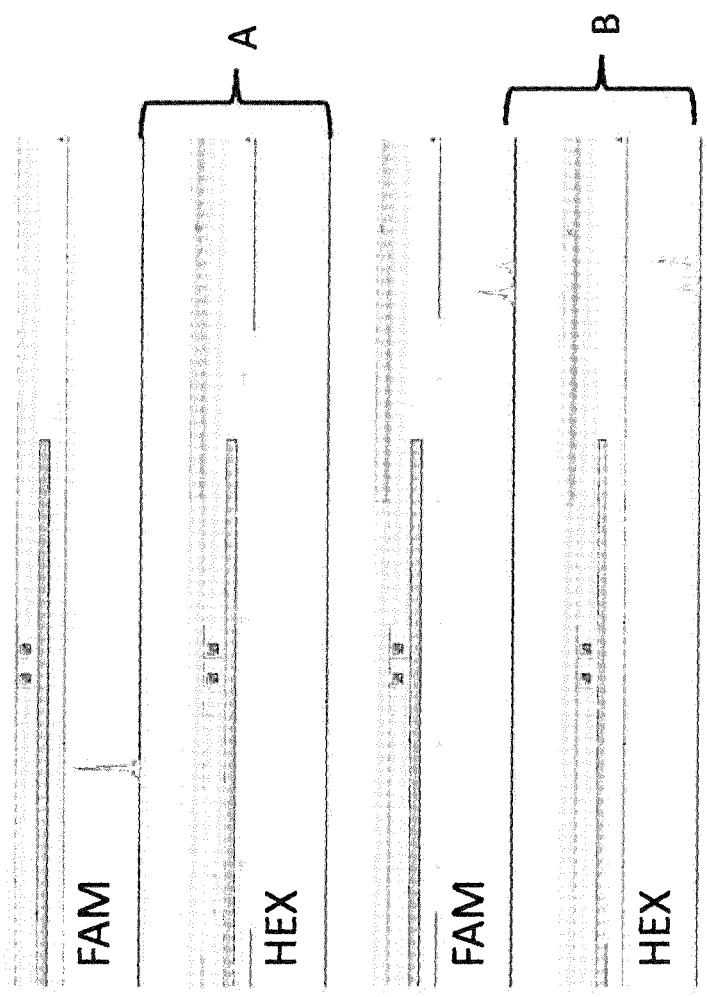
FIG. 4 shows chromatograms from detection of A) TT PCR fragments and B) ID PCR fragments, using capillary electrophoresis after use of the primer pair TT-EX14_01F/TT-EX14_02R, followed by the primer pair ID-Ion P1 and ID-Ion A.
Figure 5:
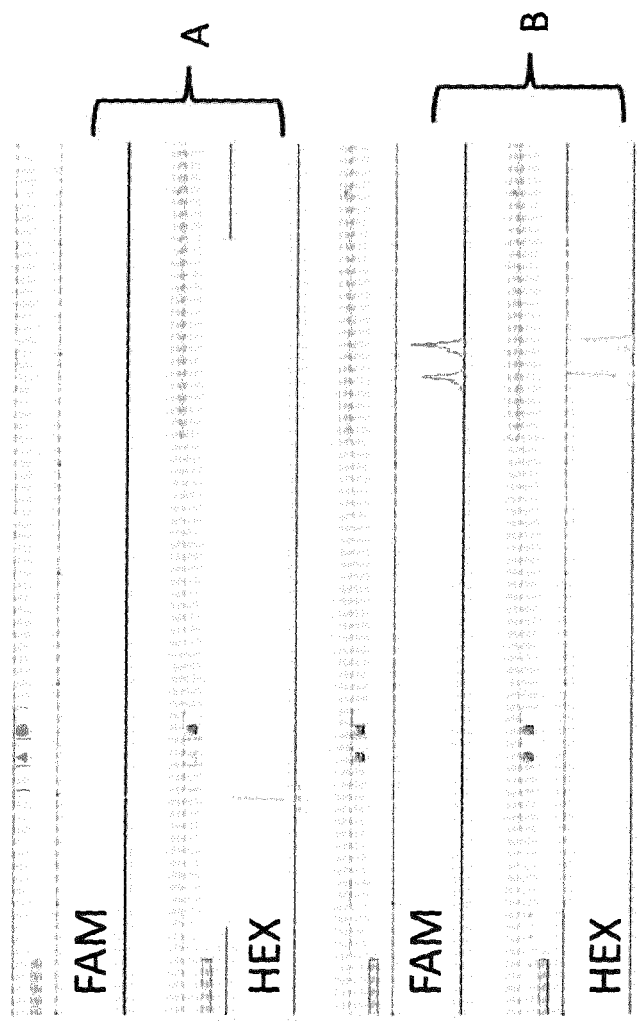
FIG. 5 shows chromatograms from detection of A) TT PCR fragments and B) ID PCR fragments, using capillary electrophoresis after use of the primer pair TT-EX14_02F/TT-EX14_03R, followed by the primer pair ID-Ion P1 and ID-Ion A.

After completion of the TT PCR reactions, the resulting solutions were diluted 50-fold, and 2 µl of the dilution were added as a template in the corresponding second stage ID PCR reaction. ID PCR was performed using the ID-Ion P1 and ID-Ion A primers. The TT and ID PCR reactions were analyzed by capillary electrophoresis detection of fluorescently labeled, amplified PCR fragments, and the chromatograms presented as FIGS. 4 and 5.

Results

For the first experiment, capillary electrophoresis of the TT PCR reaction using the primer set TT-EX14_02F/TT-EX14_02R resulted in the detection of a PCR fragment with the expected length of 180 bp in the FAM channel (FIG. 3A). However, no PCR amplicons were detected after the second stage ID PCR reaction using the resulting TT PCR product as template (FIG. 3B). The absence of detectable PCR amplicons after the combined TT and ID PCR reactions indicated that no amplification had occurred during the ID PCR.

In the second experiment, where the TT PCR primer sets TT-EX14_01F/TT-EX14_02R and TT-EX14_02F/TT-EX14_03R were used in separate TT PCR reactions, fragments with the expected fragment lengths could be observed in the FAM channel for TT primer combination TT-EX14_01F/TT-EX14_02R (FIG. 4A) and in the HEX channel for TT primer combination TT-EX14_02F/TT-EX14_03R (FIG. 5A).

Importantly, two different PCR fragments could also be detected in both the FAM and the HEX channels after the ID PCR reaction using the ID-Ion P1 and ID-Ion A primers (FIGS. 4B and 5B). The appearance of two PCR fragments in each detection channel after capillary electrophoresis of the two ID PCR reactions is in accordance with the expected four PCR fragments resulting after generic priming using two different ID PCR primers (ID-Ion P1 and ID-Ion A) that each individually is able to anneal to both ends of the TT PCR amplicons.

CONCLUSIONS

Without wishing to be bound by theory, the absence of an ID PCR product after the use of the TT-EX14_02F/TT-EX14_02R primer set was interpreted to be caused by the formation of a 15 base pairs long, self-annealing structure (which includes the generic hybridization sequence and at least two additional complementary bases) in the TT PCR amplicons. Under the PCR conditions used in this set of experiments, the self-annealing structure obstructs the annealing of the ID PCR primers to the template TT PCR amplicons during ID PCR. Conversely, when the length of the self-annealing structure is limited to only the 13 base pairs long, generic hybridization sequence in the TT PCR amplicons, annealing of ID PCR primers to the generic hybridization structure is possible. To further explain the lack of an ID PCR product from the first experiment when the primer combination was TT-EX14_02F/TT-EX14_02R, it is observed that these TT PCR primers consist of a target specific part (underlined) and a generic hybridization sequence (bold):

```
Primer TT-EX14_02F:
GCTCTTCCGATCTGCAGTCTGTCCTGAACCTGAT

Primer TT-EX14_02R:
GCTCTTCCGATCTGCCAGTTTCTTGAGATAACCTTCTTGA
```

TT PCR using TT-EX14_02F and TT-EX14_02R generates TT PCR amplicons as outlined below (with an arrow symbolizing the amplified target sequence lying between the flanking primer sequences):

```
                                    (SEQ ID NO: 1→SEQ ID NO: 7)
GCTCTTCCGATCTGCAGTCTGTCCTGAACCTGAT→TCAAGAAGGT
TATCTCAAGAAACTGGCAGATCGGAAGAGC
```

Figure 6:
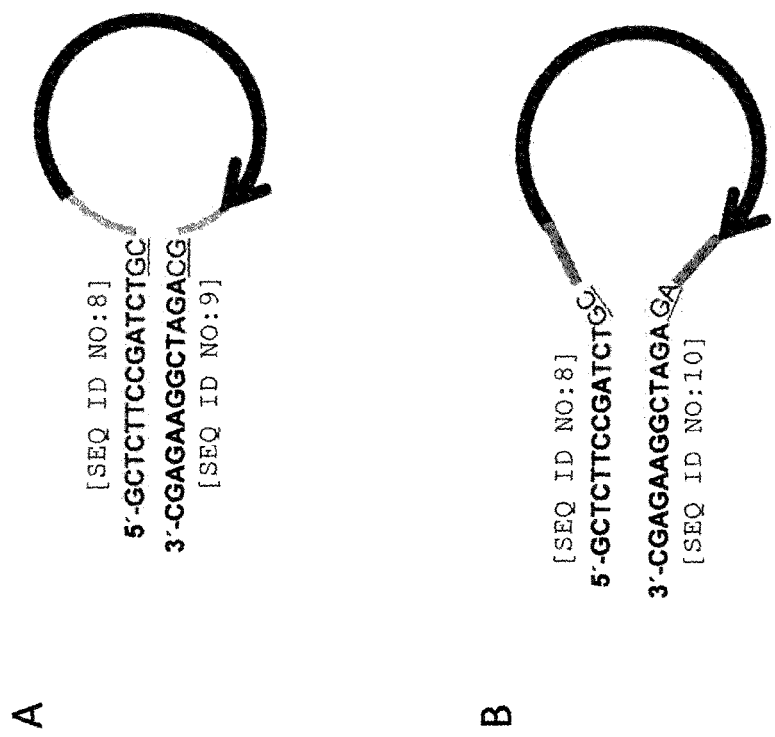
FIG. 6 is a schematic illustration of self-annealing structures of TT PCR products amplified by A) the primer pair TT-EX14_02F/TT-EX14_02R and B) the primer pair TT-EX14_02F/TT-EX14_03R. The 13 bp generic hybridization sequence is indicated in bold. The 2 bp mismatch control sequence is underlined.

This resulting TT PCR amplicon includes a self-complementary sequence in the 5' and 3' ends. Under standard PCR conditions, the self-complementary 5' and 3' ends of each amplicon self-anneal and generate a self-complementary loop structure within the amplicon. When the primer set TT-EX14_02F/TT-EX14_02R is used, the complementary region is 15 base pairs long, including the 13 bp generic hybridization sequence plus two additional complementary bases from the target specific sequence of the primers TT-EX14_02F and TT-EX14_02R (FIG. 6A). The 15 base pair self-complementary loop structure is stable enough to obstruct further PCR amplification from the amplicon during the following ID PCR, by blocking the ID PCR primer's access to the generic hybridization sequence.

The complementary regions for the TT-EX14_02F/TT-EX14_03R and TT-EX14_01F/TT-EX14_02R primer sets lack the additional complementary sequence and are only 13 base pairs long (for example the primer set TT-EX14_02F/TT-EX14_03R as shown in FIG. 6B). Under the same conditions, this stretch is not enough to generate a self-complementary loop structure stable enough to obstruct further PCR amplification from the amplicon during ID PCR.

In other words, when the self-annealing region is long enough under the conditions of the PCR experiment (in this case 15 base pairs), the self-annealed structure is favored over the annealing of an ID PCR primer (probably because of the spatial proximity of the complementary sequences at the 5' and 3' ends of the PCR product). In this case, ID PCR primers are not able to hybridize and therefore no amplification of the self-annealing TT PCR product will occur (FIGS. 3B and 6A). Conversely, when the self-annealing region is shorter, (in this case 13 base pairs), ID PCR primers are able to compete with the self-annealing structure, access the TT PCR amplicon template in order to anneal thereto. As a result, ID PCR amplification can occur (FIGS. 4B and 6B). The additional two self-complementary bases from the target specific sequences can be thought of as an intermediate sequence in between the generic hybridization sequence and the target binding region. Due to the effect this intermediate sequence has on the amplification in the second stage PCR reaction, it is denoted herein as a "mismatch control sequence", which can be designed to either allow or block the matching of additional base pairs and thus the formation of a longer, more strongly self-annealing structure than the self-annealing structure created by the generic hybridization sequence itself.

Example 2

Selection of Wanted Amplicons in Multiplex PCR

Next, it was hypothesized that in a multiplex PCR reaction using overlapping primers, mismatch control sequences or linker sequences can be included in first stage PCR primers to allow the selective formation of a self-complementary structure, and thus the formation of wanted PCR amplicons can be ensured, all the while formation of unwanted PCR amplicons is inhibited.

In order to test this hypothesis of selective self-complementary structures in an experiment, two sets of seven primer pairs each were designed following the general principles presented in Example 1. Thus, each pair of TT PCR primers was designed to overlap the first primer of the following amplicon's primer pair, in order to cover the entire exon 14 of the CFTR gene (FIG. 7).

Figure 7:
FIG. 7 is a schematic illustration of the use of overlapping PCR primers in the amplification of a stretch of target genomic DNA.
Figure 8:
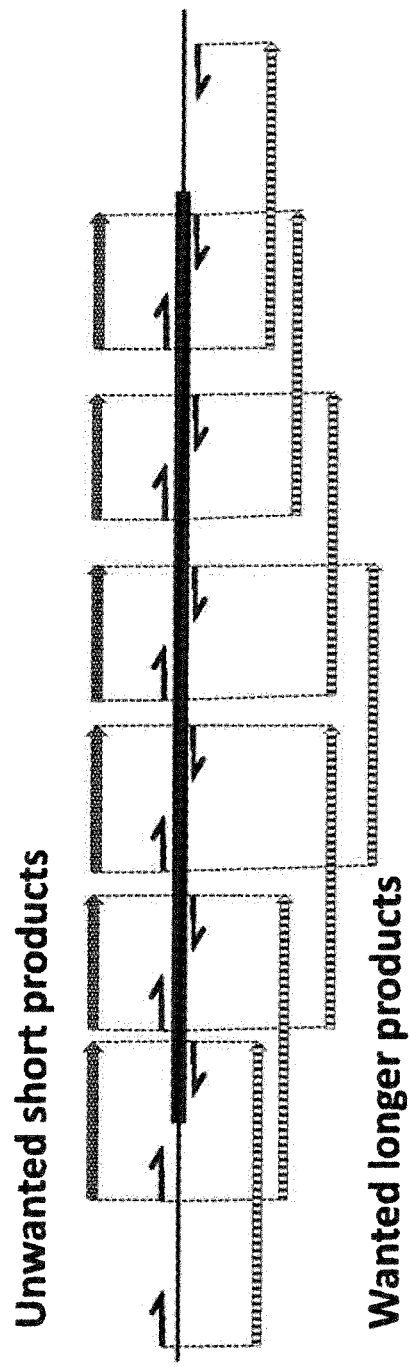
FIG. 8 is a schematic illustration of one of the problems overcome by the present method. A multitude of unwanted PCR amplicons are produced during a second stage PCR, when overlapping primers without mismatch control sequences are used during a first stage PCR.

In the first set of seven TT PCR primer pairs, the primers were designed as outlined in FIGS. 1 and 7. These primers did not include an additional mismatch control or linker sequence between the generic hybridization sequence and the target specific sequence. Thus, all amplicons arising from PCR with this primer set would be presumed to include a self-annealing region of only 13 base pairs. When combined in a single tube multiplex TT PCR reaction, a multitude of short and long TT PCR amplicons are expected (as depicted in FIG. 8).

In the second set of seven TT PCR primer pairs, the primers were identical to the first set, but a 3 bp mismatch control sequence was added between the generic hybridization sequence and the target specific sequence in each primer. The mismatch control sequences in each primer were designed (based e.g. on neighboring primers and overlap) to selectively create 16 base pairs long, self-complementary loop structures in the unwanted, shorter TT PCR amplicons, and 13 base pairs long, self-complementary loop structures in the wanted, longer TT PCR amplicons. The 16 bp self-complementary loop structures were constructed by the insertion of 3 bp self-complementary sequences in addition to the 13 bp self-complementary loop structure sequences. The two 3 bp mismatch control or linker sequences used in this experiment were:

Linker 1: 5'-GAC-3'
Linker 2: 5'-TCA-3'

Figure 9:
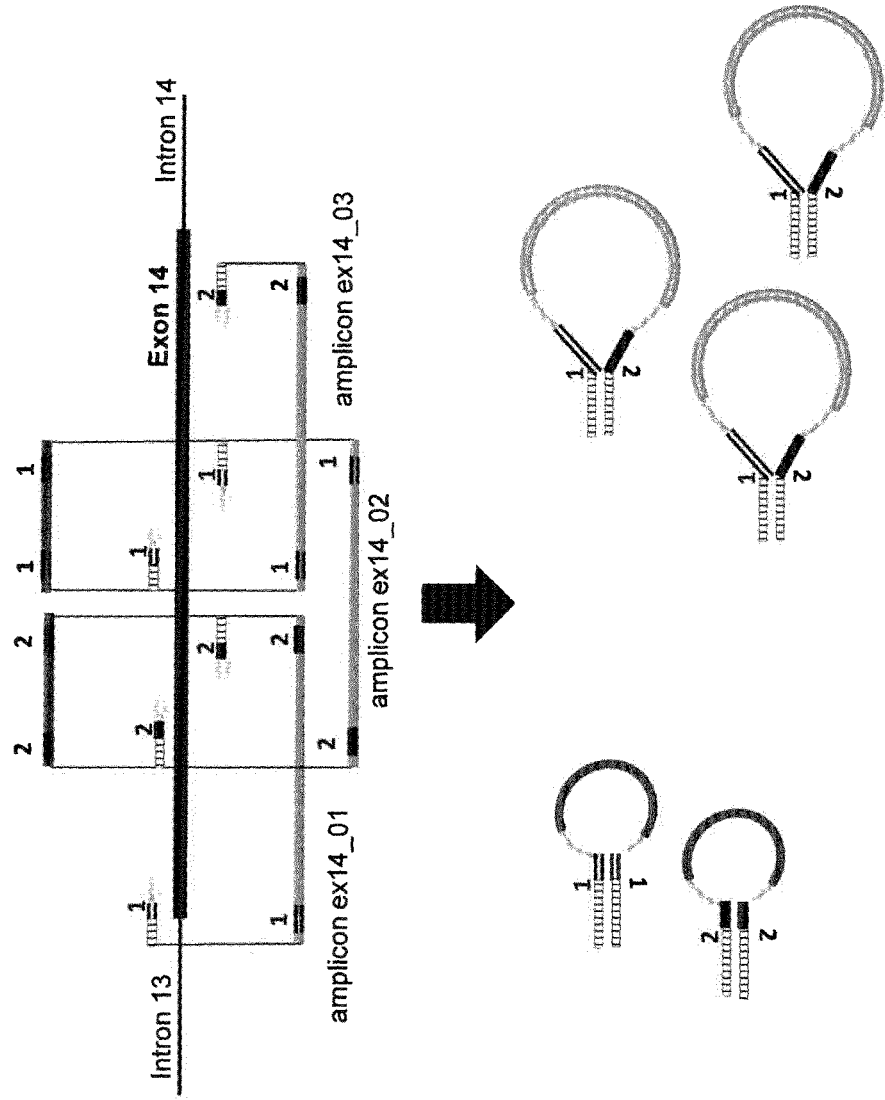
FIG. 9 is a summary schematic illustration of the disclosed method. Amplicons generated during TT PCR and having matching mismatch control sequences on both sides (1-1 or 2-2) are depicted above the target genetic sequence, and generate the longer self-complementary loop structures depicted in the lower left corner during TT PCR. Amplicons having non-matching mismatch control sequences (1-2, 2-1) are depicted below the target genetic sequence, and generate the shorter self-complementary loop structures depicted in the lower right corner during TT PCR.

The 3 bp linker sequences were positioned such as to generate longer self-complementary loop structures in the unwanted, short PCR amplicons and to generate shorter self-complementary loop structures in the longer, wanted, PCR amplicons (FIG. 9).

Figure 10:
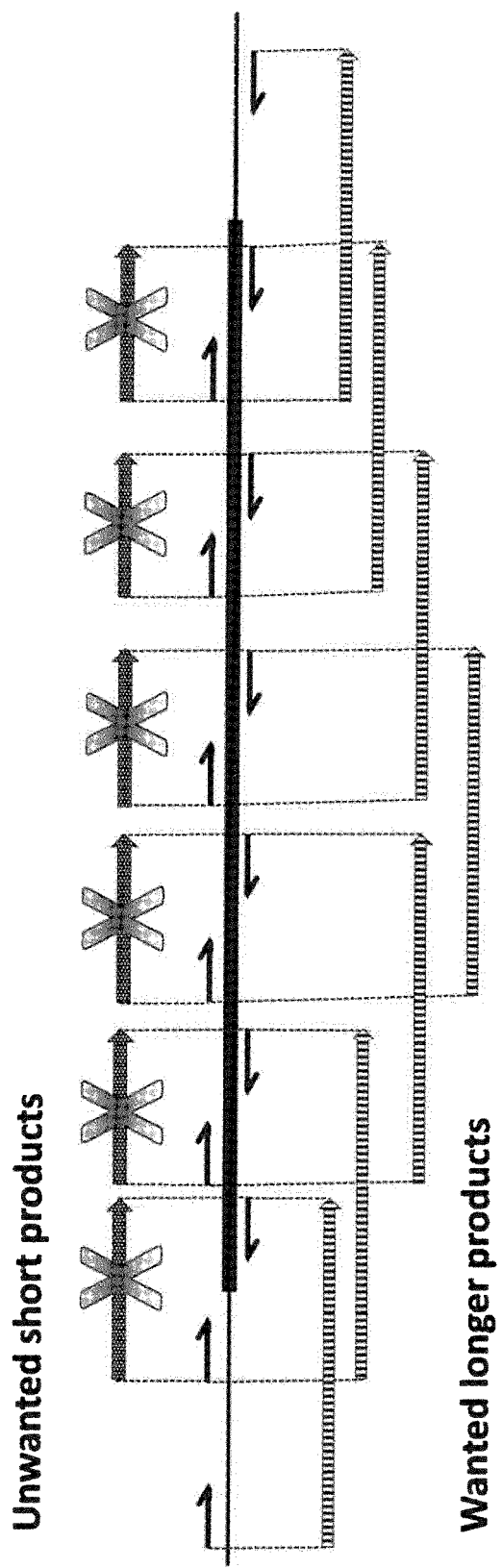
FIG. 10 is a schematic illustration of the result of the present method on the problem illustrated by FIG. 8. The inhibition of short, unwanted ID PCR amplicons during ID PCR is indicated by X.

Under suitable conditions, the formation of the longer self-complementary loop structure in a TT PCR amplicon obstructs its use as template in the subsequent ID PCR reaction, whereas the formation of the shorter self-complementary loop structure in a TT PCR amplicon allows its use as template in the subsequent ID PCR reaction. As a consequence, only specific predefined ID PCR amplicons are generated from the ID PCR reaction (FIG. 10). The principle depicted in FIGS. 7-10 was tested experimentally.

The two TT primer sets described above were used in single tube first stage multiplex TT PCR reactions, for both sets separately. Single tube multiplex TT PCR was performed on human genomic DNA for both primer sets. The resulting TT PCR amplicons were diluted 1:50 in water and then subjected to a second stage multiplex ID PCR using the ID PCR primers ID-Ion P1/ID-Ion A.

Figure 11A:
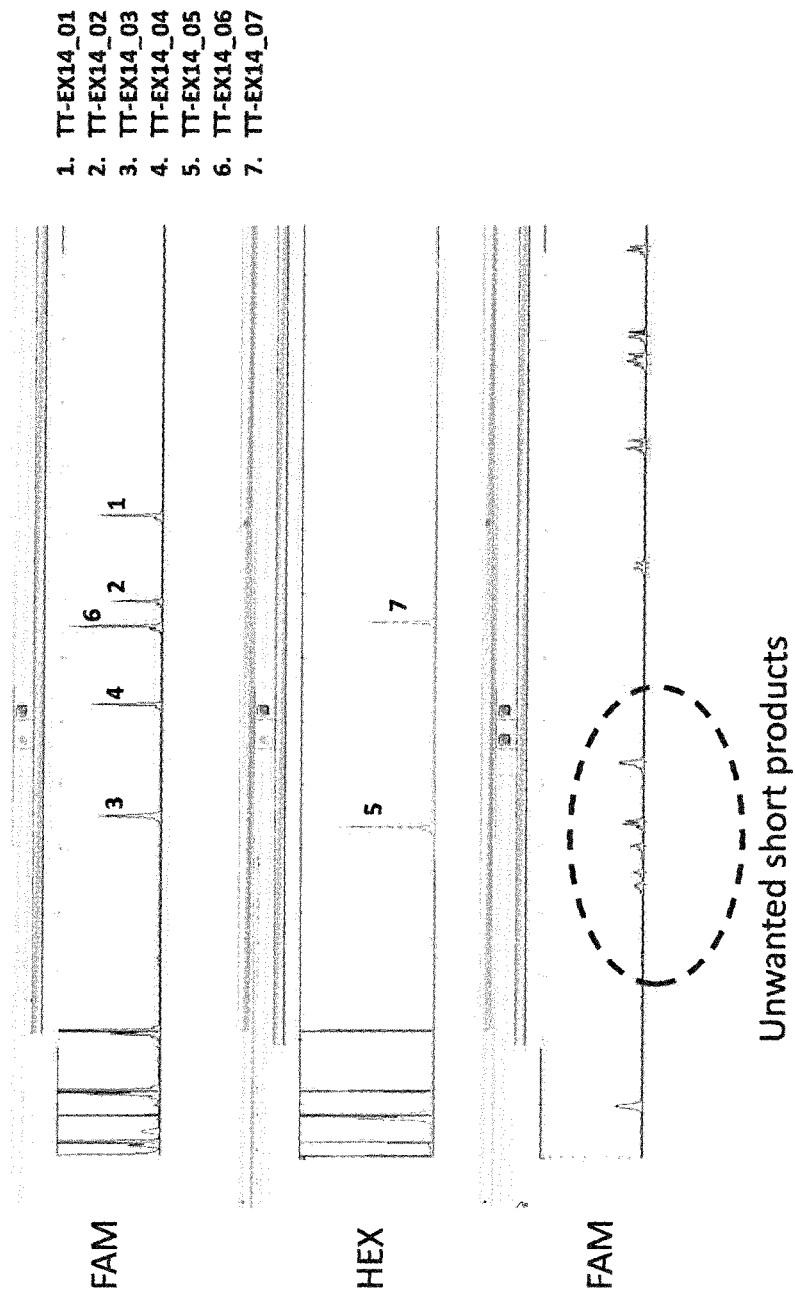
FIG. 11 shows chromatograms from capillary electrophoresis analysis after A) multiplex TT PCR (top 2 lanes) with a TT PCR primer set without mismatch control sequences, and subsequent ID PCR (bottom lane) showing a multitude of unwanted short ID PCR products; and B) multiplex TT PCR (top 2 lanes) with a TT PCR primer set including mismatch control sequences (top 2 lanes), and subsequent ID PCR (bottom lane) showing no unwanted ID PCR products.

When the primer set without designed mismatch control sequences was used, the expected 7 desired PCR amplicons were detected by capillary electrophoresis after TT PCR. In addition, a number of small, unwanted PCR products were detected (FIG. 11A, upper two lanes). The detected TT PCR amplicons all served as templates during the ID PCR reaction, generating a multitude of short unwanted ID PCR products. The formation of unwanted ID PCR amplicons was confirmed by capillary electrophoresis (FIG. 11A, lower lane).

Figure 11B:
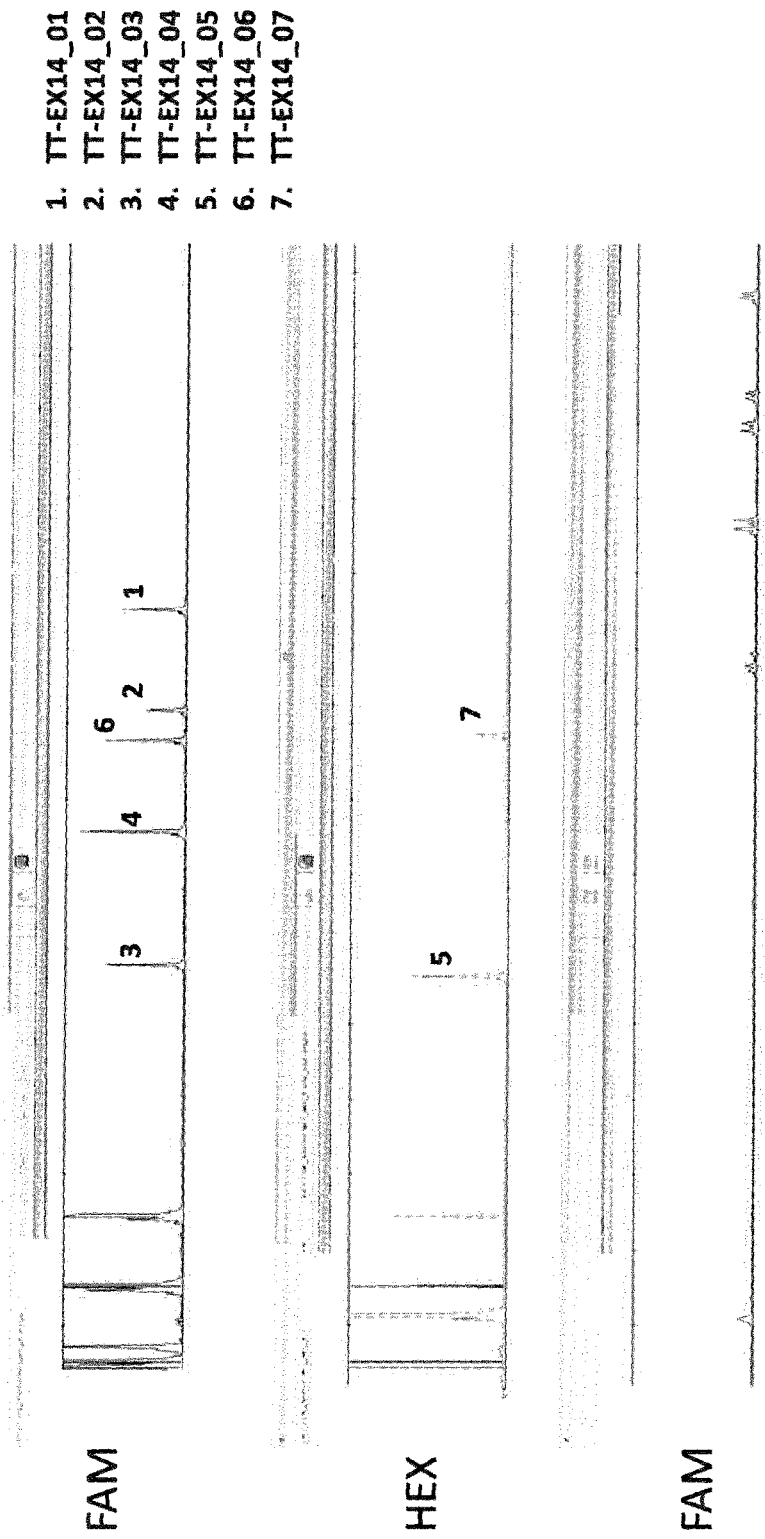

When the primer set incorporating designed mismatch control sequences was used, the expected 7 desired PCR amplicons were detected by capillary electrophoresis after the multiplex TT PCR. In addition, a number of small, unwanted PCR products were detected (FIG. 11B, upper two lanes). In this case, however, only the wanted, longer TT PCR amplicons served as templates during the ID PCR, which thus generated only the desired ID PCR products. The formation of only the wanted ID PCR amplicons was confirmed by capillary electrophoresis (FIG. 11B, lower lane).

Calculation of areas under the curve (AUC) for all peaks in the capillary electrophoresis experiments shown in FIGS. 11A and 11B, lower panels, yielded the following numbers:

|  | Without mismatch control sequences (FIG. 11A) | With mismatch control sequences (FIG. 11B) |
| --- | --- | --- |
| Total AUC: | 313457 | 101921 |
| Wanted product peaks: | 156330 | 98517 |
| Unwanted product peaks: | 157127 | 3404 |
| Percentage unwanted products: | 50% | 3% |

Example 3

Assessing Ratio of Wanted vs. Unwanted Amplification Products

Figure 12:
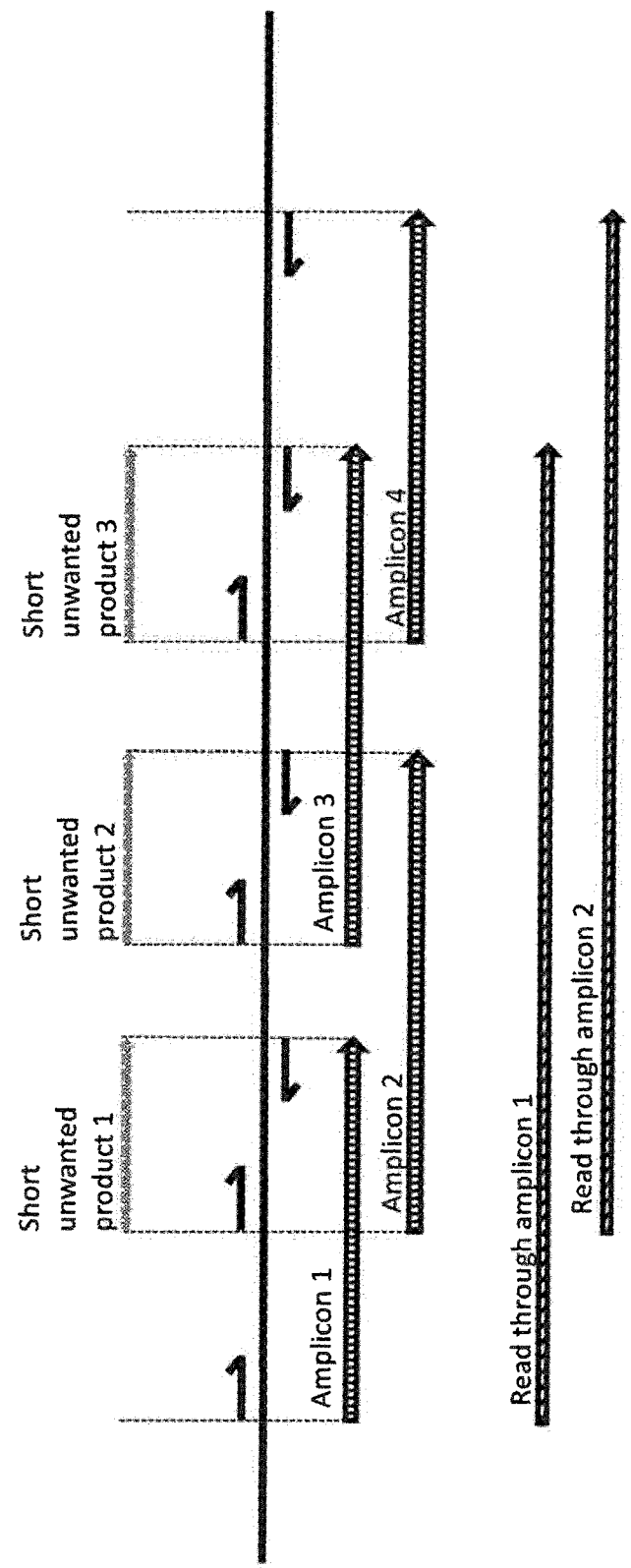
Figure 13:
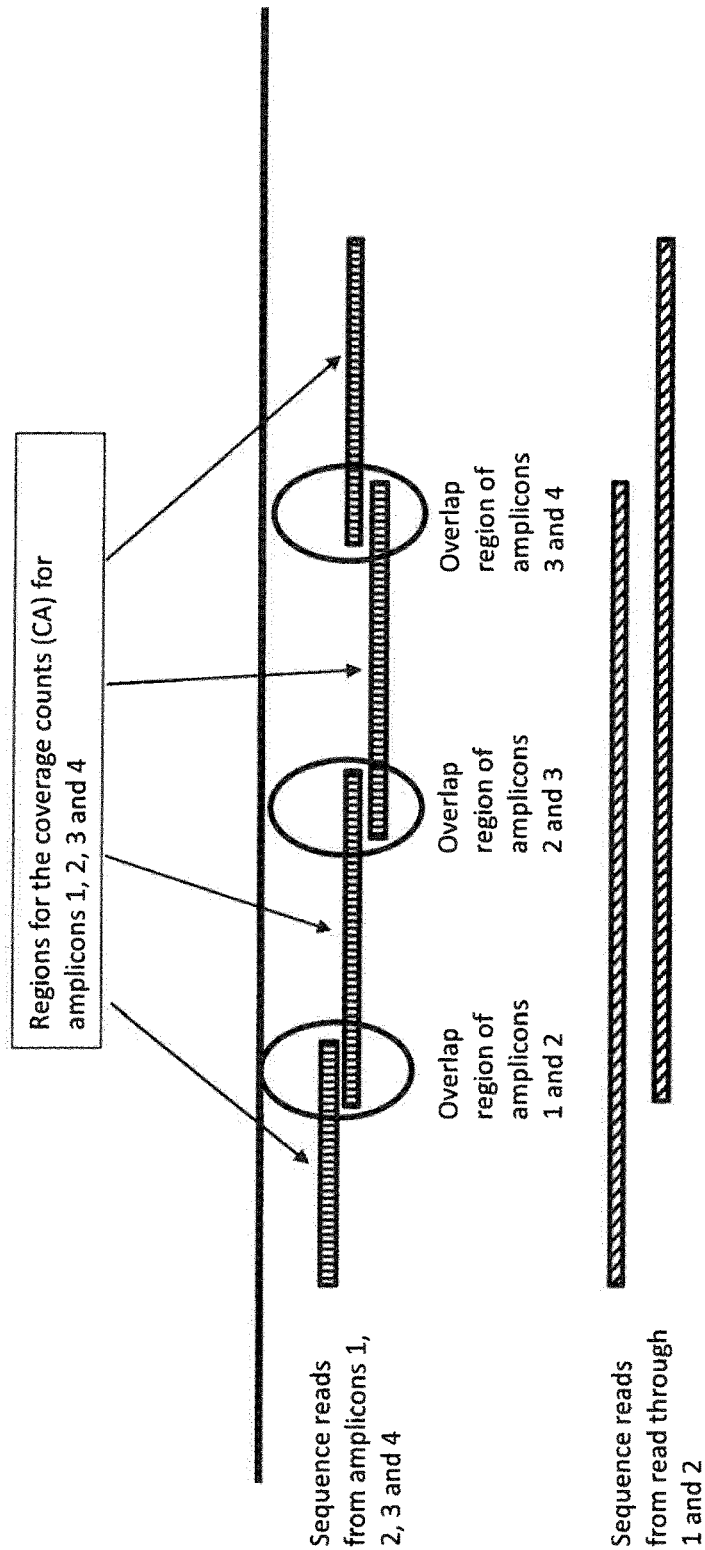
FIG. 13 illustrates schematically the regions of PCR products that are counted when calculating the parameters amplicon coverage (CA) and overlap coverage (CO) in the method described in Example 3.

To assess the amount of short, unwanted products compared to the amount of longer, wanted amplicon products in a multiplex PCR for preparation of template amplicons for next generation sequencing, the number of reads generated in the sequencing reaction for the desired amplicon region was compared to the number of reads from the overlapping region. FIG. 12 depicts an example with four amplicons covering a region of interest. In this case, during the first multiplex or "TT" PCR, three short unwanted products, four longer wanted products and two read through products are generated. The read through products are generated by the PCR interaction of the first forward primer with the third reverse primer and of the second forward primer with the fourth reverse primer, respectively. FIG. 13 shows the location of the sequence reads relative to each other after primer trimming. Amplicon count (or amplicon coverage count, CA) was generated by counting the number of reads at the marked positions for each amplicon. All reads covering these positions are specific for the assessed amplicon. Overlap region count (or coverage count for the overlapping region, CO) was generated by counting the number of reads within the overlap regions, marked by circles in FIG. 13.

If the short unwanted products generated during TT PCR are used as templates during ID PCR, the coverage of the overlapping region exceeds the sum of the coverages of the adjacent amplicons. This situation is expressed as follows:

$$CA_n + CA_{n+1} < CO_n$$

If, on the other hand, the use of mismatch control sequences in the TT PCR, as disclosed herein, prevents the short unwanted products from being used as templates during the second multiplex, or "ID" PCR, the coverage of the overlapping region should be equal to the sum of the coverages of the adjacent amplicons. This situation is expressed as follows:

$$CA_n + CA_{n+1} = CO_n$$

To determine the amount of coverage at the overlapping regions due to sequence reads from short unwanted TT PCR products, i.e. failure to form self-complementary structures and thus the formation of unwanted short amplicons in ID PCR, a coverage ratio (CR) was calculated.

$$CR = \frac{CO_n}{CA_n + CA_{n+1}}$$

A coverage ratio of 1 indicates that coverage at the overlapping regions only derives from the amplicons that form the overlap. A coverage ratio greater than 1 indicates that short unwanted TT PCR products contribute to the coverage of the overlapping region. This means that the formation of unwanted PCR amplicons during ID PCR is not inhibited as desired. In the following Examples, the coverage ratio CR is used as a measure of whether or not the method disclosed herein has the desired effect.

Example 4

39 Overlapping Amplicons of the BRCA 2 Gene

Example 2 was repeated, but using exon 11 of the BRCA 2 gene as target. The target was amplified with 39 overlapping amplicons using 78 TT PCR primers designed according to the disclosure to include mismatch control sequences of 3 bp as in Example 2. The 39 TT PCR amplicons were subjected to ID PCR as described in Example 2. The resulting library was sequenced on an Illumina MiSeq MPS instrument. The coverage ratio for each of the 39 amplicons was calculated as described in Example 3, and the results are presented in Table 2.

TABLE 2

| Amplicon | Amplicon coverage (CA) | Sum amplicon coverage ($CA_n + CA_{n+1}$) | Overlap coverage (CO) | Coverage ratio $\left(\frac{CO_n}{CA_n + CA_{n+1}}\right)$ |
| --- | --- | --- | --- | --- |
| A 1 | 690 | 1166 | 1154 | 0.99 |
| A 2 | 476 | 1254 | 1252 | 1.00 |
| A 3 | 778 | 1708 | 1670 | 0.98 |
| A 4 | 930 | 1430 | 1360 | 0.95 |

TABLE 2-continued

| Amplicon | Amplicon coverage (CA) | Sum amplicon coverage ($CA_n + CA_{n+1}$) | Overlap coverage (CO) | Coverage ratio $\left(\dfrac{CO_n}{CA_n + CA_{n+1}}\right)$ |
|---|---|---|---|---|
| A 5 | 500 | 1492 | 1446 | 0.97 |
| A 6 | 992 | 1522 | 1452 | 0.95 |
| A 7 | 530 | 1388 | 1226 | 0.88 |
| A 8 | 858 | 1474 | 1566 | 1.06 |
| A 9 | 616 | 1132 | 1120 | 0.99 |
| A 10 | 516 | 1098 | 1092 | 0.99 |
| A 11 | 582 | 1596 | 1588 | 0.99 |
| A 12 | 1014 | 1732 | 1738 | 1.00 |
| A 13 | 718 | 1508 | 1462 | 0.97 |
| A 14 | 790 | 1496 | 1462 | 0.98 |
| A 15 | 706 | 1656 | 1610 | 0.97 |
| A 16 | 950 | 1866 | 1780 | 0.95 |
| A 17 | 916 | 1740 | 1628 | 0.94 |
| A 18 | 824 | 1378 | 1342 | 0.97 |
| A 19 | 554 | 1052 | 990 | 0.94 |
| A 20 | 498 | 1456 | 1376 | 0.95 |
| A 21 | 958 | 1842 | 1718 | 0.93 |
| A 22 | 884 | 1456 | 1322 | 0.91 |
| A 23 | 572 | 1316 | 1140 | 0.87 |
| A 24 | 744 | 1598 | 1390 | 0.87 |
| A 25 | 854 | 1872 | 1744 | 0.93 |
| A 26 | 1018 | 2204 | 2218 | 1.01 |
| A 27 | 1186 | 1992 | 1940 | 0.97 |
| A 28 | 806 | 1530 | 1498 | 0.98 |
| A 29 | 724 | 1720 | 1658 | 0.96 |
| A 30 | 996 | 1682 | 1552 | 0.92 |
| A 31 | 686 | 1392 | 1314 | 0.94 |
| A 32 | 706 | 1618 | 1450 | 0.90 |
| A 33 | 912 | 1856 | 1794 | 0.97 |
| A 34 | 944 | 2018 | 1992 | 0.99 |
| A 35 | 1074 | 1568 | 1542 | 0.98 |
| A 36 | 494 | 1266 | 1228 | 0.97 |
| A 37 | 772 | 1782 | 1774 | 1.00 |
| A 38 | 1010 | 1674 | 1652 | 0.99 |
| A 39 | 664 | | | |

Table 2 shows coverage ratios for the 38 overlapping regions of the 39 amplicons used to create a sequencing library for exon 11 of the BRCA 2 gene. Only two of the 38 overlap regions have coverage ratios higher than 1.00. The highest coverage ratio, 1.06, was found for overlap region 8. This means that only 6% of the reads covering this overlap region came from unwanted short TT PCR products.

The reason why most coverage ratios are smaller than 1 is the formation of read through products which contribute unequally to the read counts of the amplicons and overlap regions respectively. This is because a read through product is counted twice for the amplicon read count CA (once for amplicon n and once for amplicon n+1), but only once for the overlap read count CO.

Example 5

31 Overlapping Amplicons of the BRCA 1 Gene

Example 2 was repeated, but using exons 10 and 11 of the BRCA 1 gene as target. The target was amplified with 31 overlapping amplicons using 62 TT PCR primers designed according to the disclosure to include mismatch control sequences of 3 bp as in Example 2. The 31 TT PCR amplicons were subjected to ID PCR as described in Example 2. The resulting library was sequenced on an Illumina MiSeq MPS instrument. The coverage ratio for each of the 31 amplicons was calculated as described in Example 3, and the results are presented in Table 3.

TABLE 3

| Amplicon | Amplicon coverage (CA) | Sum amplicon coverage ($CA_n + CA_{n+1}$) | Overlap coverage (CO) | Coverage ratio $\left(\dfrac{CO_n}{CA_n + CA_{n+1}}\right)$ |
|---|---|---|---|---|
| A 1 | 470 | 1188 | 1204 | 1.01 |
| A 2 | 718 | 1414 | 1226 | 0.87 |
| A 3 | 696 | 1538 | 1368 | 0.89 |
| A 4 | 842 | 1266 | 1186 | 0.94 |
| A 5 | 424 | 1016 | 1002 | 0.99 |
| A 6 | 592 | 1214 | 1200 | 0.99 |
| A 7 | 622 | 1334 | 1306 | 0.98 |
| A 8 | 712 | 1472 | 1424 | 0.97 |
| A 9 | 760 | 1404 | 1364 | 0.97 |
| A 10 | 644 | 1378 | 1270 | 0.92 |
| A 11 | 734 | 1494 | 1450 | 0.97 |
| A 12 | 760 | 1414 | 1380 | 0.98 |
| A 13 | 654 | 1260 | 1148 | 0.91 |
| A 14 | 606 | 1372 | 1310 | 0.95 |
| A 15 | 766 | 1244 | 1198 | 0.96 |
| A 16 | 478 | 1220 | 1186 | 0.97 |
| A 17 | 742 | 1502 | 1424 | 0.95 |
| A 18 | 760 | 1536 | 1448 | 0.94 |
| A 19 | 776 | 1582 | 1492 | 0.94 |
| A 20 | 806 | 1738 | 1656 | 0.95 |
| A 21 | 932 | 1820 | 1812 | 1.00 |
| A 22 | 888 | 1518 | 1452 | 0.96 |
| A 23 | 630 | 1526 | 1484 | 0.97 |
| A 24 | 896 | 1722 | 1680 | 0.98 |
| A 25 | 826 | 1252 | 1278 | 1.02 |
| A 26 | 426 | 1218 | 1178 | 0.97 |
| A 27 | 792 | 1312 | 1268 | 0.97 |
| A 28 | 520 | 1246 | 1156 | 0.93 |
| A 29 | 726 | 1590 | 1500 | 0.94 |
| A 30 | 864 | 1584 | 1474 | 0.93 |
| A 31 | 720 | | | |

Table 3 shows coverage ratios for the 30 overlapping regions of the 31 amplicons used to create a sequencing library for exons 10 and 11 of the BRCA 1 gene. Only two of the 30 overlap regions have coverage ratios higher than 1.00. The highest coverage ratio, 1.02, was found for overlap region 25. This means that only 2% of the reads covering this overlap region came from unwanted short TT PCR products.

Example 6

7 Overlapping Amplicons of the CFTR Gene

Example 2 was repeated. The target was amplified with 7 overlapping amplicons using 14 TT PCR primers designed according to the disclosure to include mismatch control sequences of 3 bp as in Example 2. The 7 TT PCR amplicons were subjected to ID PCR as described in Example 2. The resulting library was sequenced on an Illumina MiSeq MPS instrument. The coverage ratio for each of the 7 amplicons was calculated as described in Example 3, and the results are presented in Table 4.

TABLE 4

| Amplicon | Amplicon coverage (CA) | Sum amplicon coverage ($CA_n + CA_{n+1}$) | Overlap coverage (CO) | Coverage ratio $\left(\dfrac{CO_n}{CA_n + CA_{n+1}}\right)$ |
|---|---|---|---|---|
| A1 | 148 | 218 | 220 | 1.01 |
| A2 | 70 | 958 | 940 | 0.98 |
| A3 | 888 | 1348 | 1250 | 0.93 |
| A4 | 460 | 966 | 922 | 0.95 |
| A5 | 506 | 936 | 902 | 0.96 |
| A6 | 430 | 830 | 824 | 0.99 |
| A7 | 400 | | | |

Table 4 shows the coverage ratios for the 6 overlapping regions of the 7 amplicons used to create a sequencing library for exon 14 of the CFTR gene. Only two of the 7 overlap regions have coverage ratios higher than 1.00. The highest coverage ratio, 1.01, was found for overlap region 1. This means that only 1% of the reads covering this overlap region come from unwanted short TT PCR products.

Example 7

7 Overlapping Amplicons of the TP53 Gene

Example 2 was repeated, but using exons 4 and 5 of the TP53 gene as target. The target was amplified with 7 overlapping amplicons using 14 TT PCR primers designed according to the disclosure to include mismatch control sequences of 3 bp as in Example 2. The 7 TT PCR amplicons were subjected to ID PCR as described in Example 2. The resulting library was sequenced on an Illumina MiSeq MPS instrument. The coverage ratio for each of the 7 amplicons was calculated as described in Example 3, and the results are presented in Table 5.

TABLE 5

| Amplicon | Amplicon coverage (CA) | Sum amplicon coverage ($CA_n + CA_{n+1}$) | Overlap coverage (CO) | Coverage ratio $\left(\dfrac{CO_n}{CA_n + CA_{n+1}}\right)$ |
|---|---|---|---|---|
| A1 | 1798 | 5276 | 4486 | 0.85 |
| A2 | 3478 | 6612 | 5622 | 0.85 |
| A3 | 3134 | 5462 | 3850 | 0.70 |
| A4 | 2328 | 4584 | 3256 | 0.71 |
| A5 | 2256 | 4846 | 4404 | 0.91 |
| A6 | 2590 | 4208 | 4008 | 0.95 |
| A7 | 1618 | | | |

Table 5 shows the coverage ratios for the 6 overlapping regions of the 7 amplicons used to create a sequencing library for exons 4 and 5 of the TP53 gene. None of the 7 overlap regions has a coverage ratio higher than 1.00, indicating that no unwanted short TT PCR products were formed.

Example 8

5 Overlapping Amplicons of the KIT Gene

Example 2 was repeated, but using exons 12 and 13 of the KIT gene as target. The target was amplified with 5 overlapping amplicons using 10 TT PCR primers designed according to the disclosure to include mismatch control sequences of 3 bp as in Example 2. The 5 TT PCR amplicons were subjected to ID PCR as described in Example 2. The resulting library was sequenced on an Illumina MiSeq MPS instrument. The coverage ratio for each of the 5 amplicons was calculated as described in Example 3, and the results are presented in Table 6.

TABLE 6

| Amplicon | Amplicon coverage (CA) | Sum amplicon coverage ($CA_n + CA_{n+1}$) | Overlap coverage (CO) | Coverage ratio $\left(\dfrac{CO_n}{CA_n + CA_{n+1}}\right)$ |
|---|---|---|---|---|
| A1 | 706 | 1702 | 1638 | 0.96 |
| A2 | 996 | 1936 | 1728 | 0.89 |
| A3 | 940 | 1952 | 1792 | 0.92 |
| A4 | 1012 | 1772 | 1724 | 0.97 |
| A5 | 760 | | | |

Table 6 shows the coverage ratios for the 5 overlapping regions of the 6 amplicons used to create a sequencing library for exons 12 and 13 of the TP53 gene. None of the 5 overlap regions has a coverage ratio higher than 1.00, indicating that no unwanted short TT PCR products were formed.

Example 9

3 Overlapping Amplicons of the PDGFRA Gene

Example 2 was repeated, but using exon 12 of the PDGFRA gene as target. The target was amplified with 3 sequences of 3 bp as in Example 2. The 3 TT PCR amplicons were subjected to ID PCR as described in Example 2. The resulting library was sequenced on an Illumina MiSeq MPS instrument. The coverage ratio for each of the 3 amplicons was calculated as described in Example 3, and the results are presented in Table 7. overlapping amplicons using 6 TT PCR primers designed according to the disclosure to include mismatch control Table 7 shows the coverage ratios for the 2 overlapping regions of the 3 amplicons used to create a sequencing library for exon 12 of the PDGFRA gene. None of the 2 overlap regions has a coverage ratio higher than 1.00, indicating that no unwanted short TT PCR products were formed.

TABLE 7

| Amplicon | Amplicon coverage (CA) | Sum amplicon coverage $(CA_n + CA_{n+1})$ | Overlap coverage (CO) | Coverage ratio $\left(\dfrac{CO_n}{CA_n + CA_{n+1}}\right)$ |
|---|---|---|---|---|
| A1 | 451 | 1068 | 1006 | 0.94 |
| A2 | 617 | 1539 | 1472 | 0.96 |
| A3 | 922 | | | |

The invention claimed is:

1. A method for selective amplification of desired amplicons in a two-stage polymerase chain reaction, comprising the steps of:
   providing a target genetic material;
   denaturing the target genetic material;
   adding a set of target primers under conditions allowing annealing of primers to the target genetic material;
      each primer in said set of target primers comprising
         a target specific sequence,
         a mismatch control sequence, and
         a generic hybridization sequence;
      said generic hybridization sequence being identical in each target primer;
      said mismatch control sequence and generic hybridization sequence being in close proximity to each other; and
      said set of target primers comprising at least two primer pairs adapted for amplification of at least two overlapping desired amplicons in the target genetic material, such that there is a possibility of obtaining at least one undesired amplicon in the region of overlap;
      said set of target primers being further characterized in that any pair of primers that flank a desired amplicon sequence have non-matching mismatch control sequences, while any pair of primers that flank an undesired amplicon sequence have matching mismatch control sequences;
   carrying out a first multiplex polymerase chain reaction resulting in overlapping amplicons corresponding to different possible pair-wise combinations of primers in the first set of primers, said overlapping amplicons being maintained under conditions such that they self-hybridize through base-pair coupling between the complementary sequences resulting from the generic hybridization sequence in each primer;
   treating said overlapping amplicons under selection conditions that are such that desired amplicons denature because of non-complementary sequences resulting from the non-matching mismatch control sequences, while undesired amplicons stay self-hybridized because of additional complementary sequences resulting from the matching mismatch control sequences;
   adding generic primers, each comprising a sequence which is complementary to the generic hybridization sequence;
   carrying out a second polymerase chain reaction, resulting in the selective amplification of desired amplicons.

2. The method according to claim 1, wherein said first and second polymerase chain reactions are carried out in different reaction vessels.

3. The method according to claim 2, wherein said target primers are added before said first multiplex polymerase chain reaction, and said generic primers are added after said first multiplex polymerase chain reaction and before said second polymerase chain reaction.

4. The method according to claim 1, wherein said first and second polymerase chain reactions are carried out in the same reaction vessel.

5. The method according to claim 4, wherein said target primers and generic primers are added before said first multiplex polymerase chain reaction.

6. The method according to claim 1, wherein the total length of a target primer in said set of target primers is in the range from about 7 to about 200 nucleotides.

7. The method according to claim 1, wherein the length of said mismatch control sequence is in the range from 1 to 7 nucleotides.

8. The method according to claim 1, wherein the length of said generic hybridization sequence is in the range from 1 to 75 nucleotides.

9. The method according to claim 1, wherein the length of said target specific sequence is in the range from 5 to 100 nucleotides.

10. The method according to claim 1, wherein at least one primer in at least one pair is detectably labeled.

11. The method according to claim 1, wherein said generic primers further comprise adapter sequences for sequencing said desired amplicons.

12. The method according to claim 11, further comprising a step of sequencing said desired amplicons.

13. The method according to claim 12, wherein said sequencing is carried out using massively parallel sequencing.

14. The method according to claim 1, wherein said generic primers further comprise index sequences.

15. The method according to claim 1, wherein at least one target primer is complementary to a diagnostic sequence in the target genetic material.

16. A kit for selective amplification of desired amplicons in a two-stage polymerase chain reaction, comprising:
   a set of target primers;
      each primer in said set of target primers comprising
         a target specific sequence,
         a mismatch control sequence, and
         a generic hybridization sequence;
      said generic hybridization sequence being identical in each target primer;
      said mismatch control sequence and generic hybridization sequence being in close proximity to each other; and
      said set of target primers comprising at least two primer pairs adapted for amplification of at least two overlapping desired amplicons in a target genetic material, such that there is a possibility of obtaining at least one undesired amplicon in the region of overlap;
      said set of target primers being further characterized in that any pair of primers that flank a desired amplicon sequence have non-matching mismatch control sequences, while any pair of primers that flank an undesired amplicon sequence have matching mismatch control sequences;
   generic primers, each comprising a sequence which is complementary to the generic hybridization sequence; and
   instructions for carrying out the method according to claim 1 using said primers.

17. The kit according to claim 16, wherein the total length of a target primer in said set of target primers is in the range from about 7 to about 200 nucleotides.

* * * * *

SEQUENCE LISTING

<160> NUMBER OF SEQ ID NOS: 10

<210> SEQ ID NO 1
<211> LENGTH: 34
<212> TYPE: DNA
<213> ORGANISM: ARTIFICIAL SEQUENCE
<220> FEATURE:
<223> OTHER INFORMATION: Engineered oligonucleotide primer for PCR

<400> SEQUENCE: 1
gctcttccga tctgcagtct gtcctgaacc tgat                     34

<210> SEQ ID NO 2
<211> LENGTH: 40
<212> TYPE: DNA
<213> ORGANISM: ARTIFICIAL SEQUENCE
<220> FEATURE:
<223> OTHER INFORMATION: Engineered oligonucleotide primer for PCR

<400> SEQUENCE: 2
gctcttccga tctgccagtt tcttgagata accttcttga               40

<210> SEQ ID NO 3
<211> LENGTH: 38
<212> TYPE: DNA
<213> ORGANISM: ARTIFICIAL SEQUENCE
<220> FEATURE:
<223> OTHER INFORMATION: Engineered oligonucleotide primer for PCR

<400> SEQUENCE: 3
gctcttccga tctttccatt gtgcaaaaga ctccctta                 38

<210> SEQ ID NO 4
<211> LENGTH: 41
<212> TYPE: DNA
<213> ORGANISM: ARTIFICIAL SEQUENCE
<220> FEATURE:
<223> OTHER INFORMATION: Engineered oligonucleotide primer for PCR

<400> SEQUENCE: 4
gctcttccga tctggaagag atatgtccat tgcaaaaaga a                                41

<210> SEQ ID NO 5
<211> LENGTH: 54
<212> TYPE: DNA
<213> ORGANISM: ARTIFICIAL SEQUENCE
<220> FEATURE:
<223> OTHER INFORMATION: Engineered oligonucleotide primer for PCR

<400> SEQUENCE: 5
ccactacgcc tccgctttcc tctctatggg cagtcggtga tgctcttccg atct            54

<210> SEQ ID NO 6
<211> LENGTH: 55
<212> TYPE: DNA
<213> ORGANISM: ARTIFICIAL SEQUENCE
<220> FEATURE:
<223> OTHER INFORMATION: Engineered oligonucleotide primer for PCR

<400> SEQUENCE: 6
ccatctcatc cctgcgtgtc tccgactcac agaaggaacg atgctcttcc gatct           55

<210> SEQ ID NO 7
<211> LENGTH: 40
<212> TYPE: DNA
<213> ORGANISM: ARTIFICIAL SEQUENCE
<220> FEATURE:
<223> OTHER INFORMATION: 3' end of PCR amplicon using TT-EX14_02F and
      TT-EX14_02R as PCR primers

<400> SEQUENCE: 7
tcaagaaggt tatctcaaga aactggcaga tcggaagagc                             40

<210> SEQ ID NO 8
<211> LENGTH: 15
<212> TYPE: DNA
<213> ORGANISM: ARTIFICIAL SEQUENCE
<220> FEATURE:
<223> OTHER INFORMATION: 5' part of amplicons illustrated in Figure 6A
      and 6B

<400> SEQUENCE: 8
gctcttccga tctgc                                                        15

<210> SEQ ID NO 9
<211> LENGTH: 15
<212> TYPE: DNA
<213> ORGANISM: ARTIFICIAL SEQUENCE
<220> FEATURE:
<223> OTHER INFORMATION: 3' part of amplicon illustrated in Figure 6A

<400> SEQUENCE: 9
gcagatcgga agagc                                                        15

<210> SEQ ID NO 10
<211> LENGTH: 15
<212> TYPE: DNA
<213> ORGANISM: ARTIFICIAL SEQUENCE
<220> FEATURE:
<223> OTHER INFORMATION: 3' part of amplicon illustrated in Figure 6B

<400> SEQUENCE: 10
agagatcgga agagc                                                        15